US010726702B2

(12) United States Patent
Yamawaki et al.

(10) Patent No.: US 10,726,702 B2
(45) Date of Patent: Jul. 28, 2020

(54) INFORMATION PROCESSING SYSTEM, INFORMATION PROCESSING METHOD, AND PROGRAM

(71) Applicant: Rakuten, Inc., Tokyo (JP)

(72) Inventors: Nozomi Yamawaki, Tokyo (JP); Makoto Komatsu, Tokyo (JP)

(73) Assignee: Rakuten, Inc., Setagaya-ku, Tokyo (JP)

( * ) Notice: Subject to any disclaimer, the term of this patent is extended or adjusted under 35 U.S.C. 154(b) by 0 days.

(21) Appl. No.: 16/313,692

(22) PCT Filed: Jul. 5, 2016

(86) PCT No.: PCT/JP2016/069918
§ 371 (c)(1),
(2) Date: Dec. 27, 2018

(87) PCT Pub. No.: WO2018/008090
PCT Pub. Date: Jan. 11, 2018

(65) Prior Publication Data
US 2019/0251824 A1 Aug. 15, 2019

(51) Int. Cl.
G08B 21/24 (2006.01)
A61B 5/00 (2006.01)
(Continued)

(52) U.S. Cl.
CPC .......... *G08B 21/24* (2013.01); *A61B 5/01* (2013.01); *A61B 5/4806* (2013.01); (Continued)

(58) Field of Classification Search
CPC ........ G08B 21/24; G08B 21/182; A61B 5/01; A61B 5/4809
See application file for complete search history.

(56) References Cited

U.S. PATENT DOCUMENTS 6,773,726 B2 * 8/2004 Sweazy .................. A23L 33/30
424/670
10,060,802 B1 * 8/2018 Ragosta ............... G01K 13/002
(Continued)

FOREIGN PATENT DOCUMENTS

JP 2926049 B1 7/1999
JP 2012-220287 A 11/2012
(Continued)

OTHER PUBLICATIONS

International Search Report for PCT/JP2016/069918 dated Sep. 20, 2016 [PCT/ISA/210].

*Primary Examiner* — Brian A Zimmerman
*Assistant Examiner* — Kevin Lau
(74) *Attorney, Agent, or Firm* — Sughrue Mion, PLLC

(57) ABSTRACT

Provided is an information processing system capable of effectively preventing a user's failure to take his or her basal body temperature.
The base time setter 301 sets, as a base measurement time, a time used as a basis for a user to take the user's body temperature after awakening, based on the times at which the user's body temperatures were measured. The sleep duration estimator 302 estimates the user U's most recent sleep duration. When the user's most recent sleep duration exceeds a predetermined threshold value, the alarm controller 303 causes an alarm to sound at the base measurement time.

11 Claims, 8 Drawing Sheets

(51) Int. Cl.
*G01K 7/00* (2006.01)
*A61B 5/01* (2006.01)
*G08B 21/18* (2006.01)

(52) U.S. Cl.
CPC ............ *A61B 5/4809* (2013.01); *A61B 5/746* (2013.01); *G01K 7/00* (2013.01); *G08B 21/182* (2013.01)

(56) References Cited

U.S. PATENT DOCUMENTS

| | | | |
|---|---|---|---|
| 2012/0238900 A1* | 9/2012 | Rechberg | A61B 5/01 600/549 |
| 2015/0145693 A1 | 5/2015 | Toriumi et al. | |
| 2015/0289768 A1 | 10/2015 | Toriumi et al. | |
| 2016/0284200 A1* | 9/2016 | Song | G06F 3/03546 |
| 2017/0094046 A1* | 3/2017 | Raymann | H04W 4/70 |
| 2018/0214028 A1* | 8/2018 | Zhang | G01K 1/14 |
| 2019/0045046 A1* | 2/2019 | Ma | H04M 1/571 |

FOREIGN PATENT DOCUMENTS

| | | |
|---|---|---|
| WO | 2014/115325 A1 | 7/2014 |
| WO | 2014/155605 A1 | 10/2014 |

\* cited by examiner

| DATE | MEASUREMENT TIME | BASAL BODY TEMPERATURE |
|---|---|---|
| MONDAY, JUNE 6 | 7:05 | 36.5 |
| TUESDAY, JUNE 7 | 7:04 | 36.3 |
| WEDNESDAY, JUNE 8 | 7:08 | 36.4 |
| THURSDAY, JUNE 9 | 6:55 | 36.5 |
| FRIDAY, JUNE 10 | 6:50 | 36.6 |
| SATURDAY, JUNE 11 | 7:13 | 36.6 |
| SUNDAY, JUNE 12 | 6:45 | 36.4 |

| BASE MEASUREMENT TIME |
|---|
| 7:00 |

| ALARM ID | ALARM TIME | ON/OFF |
|---|---|---|
| 0001 | EVERY MORNING 7:00 | ON |
| 0002 | 7:20 | OFF |
| 0003 | 5:30 | OFF |

| ALARM ID | ALARM TIME | ON/OFF |
|---|---|---|
| 0001 | EVERY MORNING 7:00 | OFF |
| 0002 | 7:20 | ON |
| 0003 | 5:30 | OFF |

INFORMATION PROCESSING SYSTEM, INFORMATION PROCESSING METHOD, AND PROGRAM

CROSS REFERENCE TO RELATED APPLICATIONS

This application is a National Stage of International Application No. PCT/JP2016/069918, filed on Jul. 5, 2016.

TECHNICAL FIELD

The present invention relates to an information processing system, an information processing method, and a program.

BACKGROUND ART

As conventionally known, there exist a basal thermometer that keeps track of a user's basal body temperatures in cooperation with, for example, a smartphone (e.g., see Patent Literature 1).

A user who uses this basal thermometer wakes up at a set alarm time every morning and takes the basal body temperature.

However, the user may fail to take the basal body temperature if the user forgets to set an alarm.

For this reason, Patent Literature 2, for example, discloses a technique for sounding an alarm when a user fails to take the basal body temperature for several days in a row.

CITATION LIST

Patent Literature

Patent Literature 1: JP 2012-220287 A
Patent Literature 2: JP 2926049 B

SUMMARY OF INVENTION

Technical Problem

However, the conventional technique disclosed in Patent Literature 2 causes an alarm to sound to a user after the user fails to take the basal body temperature for several days in a row, and thus cannot prevent the user's failure to take the basal body temperature.

In view of such a situation, it is an object of the present invention to effectively prevent a user's failure to take the basal body temperature.

Solution to Problem

To achieve the above object, an information processing system according to an aspect of the present invention includes base time setting means, sleep duration estimation means, and alarm control means.

The base time setting means sets, as a base measurement time, a time used as a basis for a user to take the user's body temperature after awakening, based on the times at which the user's body temperatures were measured.

The sleep duration estimation means estimates the user's most recent sleep duration.

When the user's most recent sleep duration exceeds a predetermined threshold value, the alarm control means causes an alarm to sound at the base measurement time.

The sleep duration estimation means can estimate the sleep duration to be the time interval between the user's most recent operation on the user's mobile terminal and the base measurement time.

When no operation is performed on the user's mobile terminal for a predetermined duration of time, the sleep duration estimation means further estimates that the user is in a sleeping state.

If an operation is performed on the mobile terminal before the base measurement time in the sleeping state, the alarm control means can cancel a process for causing an alarm to sound at the base measurement time.

Alternatively, when no operation is performed on the user's mobile terminal for a predetermined duration of time, the sleep duration estimation means further estimates that the user is in a sleeping state.

When an operation is performed on the mobile terminal before the base measurement time in the sleeping state, the alarm control means can cause an alarm to sound if the user's most recent sleep duration exceeds a predetermined threshold value at that point, and cancel a process for causing an alarm to sound at the base measurement time if the user's most recent sleep duration is below a predetermined threshold value at that point.

If the sleep duration is below the predetermined threshold value at the base measurement time, the alarm control means can further cause an alarm to sound at a predetermined time that is the time when the user's most recent sleep duration will exceed a predetermined threshold value or after.

If an operation is performed on the mobile terminal before the predetermined time in the sleeping state, the alarm control means can cancel a process for causing an alarm to sound at the predetermined time.

After setting the base measurement time, the base time setting means can further perform a process for resetting the base measurement time at a predetermined timing.

The base time setting means can set the base measurement time, based on measurement times included in measurement logs for a user's body temperatures after awakening that were regularly measured.

The base time setting means can set, as the base measurement time, a time that is a predetermined period of time or more after a base time found based on the measurement times. The predetermined period of time is determined based on the average value or the mode value of the measurement times and on the standard deviation of the measurement times.

Whether to sound the alarm is managed using sets of data each including a predetermined identifier, an alarm time, and status information indicating that the alarm is ON or OFF.

If the sets already managed include a set having an alarm time that is the same as the base measurement time, the alarm control means can change the status information included in the set to ON.

An information processing method and a program according to an aspect of the present invention correspond to the above information processing system according to an aspect of the present invention.

Advantageous Effects of Invention

The present invention can effectively prevent a user's failure to take the basal body temperature.

DESCRIPTION OF EMBODIMENTS

The following describes an embodiment of the present invention with reference to the drawings.

Figure 1:
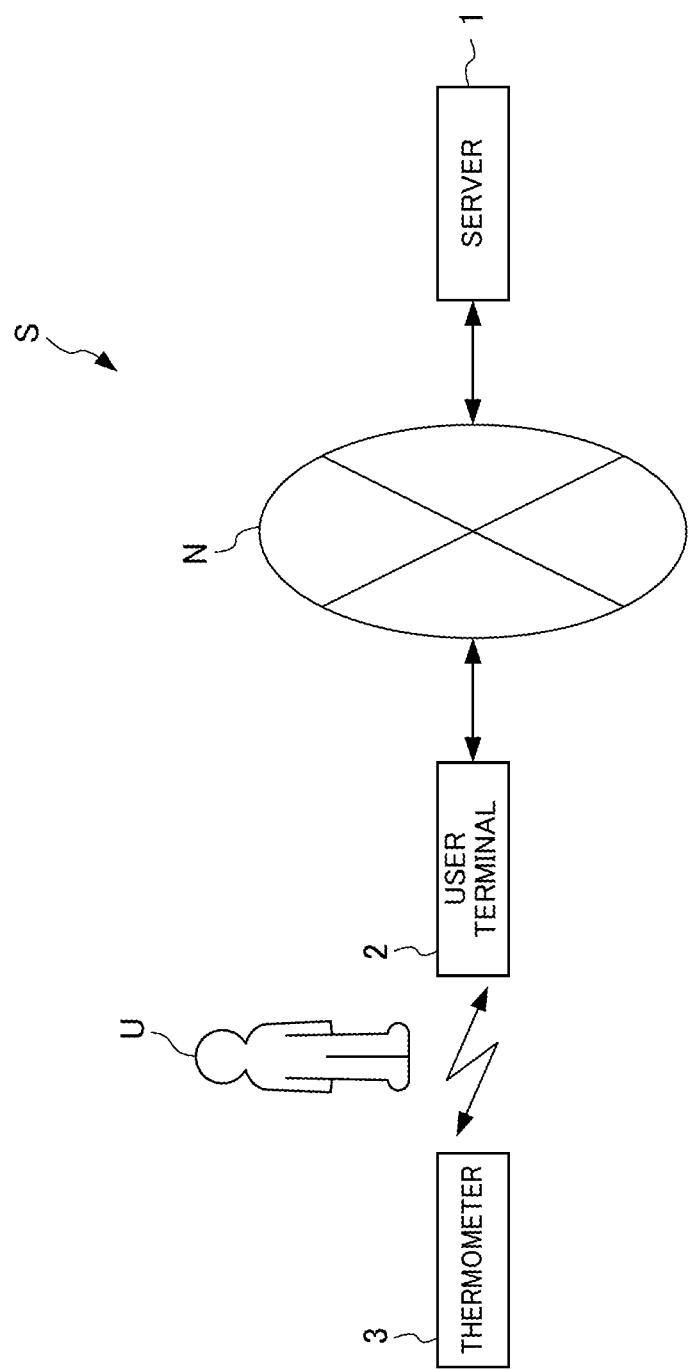
FIG. 1 is a diagram showing a general configuration of an information processing system according to an embodiment of the present invention.

FIG. 1 is a diagram showing a general configuration of an information processing system S according to an embodiment of the present invention.

The information processing system S shown in FIG. 1 includes a server 1, a user terminal 2, and a thermometer 3.

The server 1 and user terminal 2 exchange various types of information with each other over a predetermined network N, such as the Internet.

The user terminal 2 and the thermometer 3 exchange various types of information via predetermined communication means. The predetermined communication means is not particularly limited. For example, this embodiment uses Bluetooth® as wireless communication means.

The server 1 performs various processes to manage operations of the user terminal 2.

The user terminal 2 is an information processing device operated by a user U. For example, the user terminal 2 is a smartphone in this embodiment.

The thermometer 3 measures the user U's basal body temperature and sends the measurement to the user terminal 2.

FIG. 1 shows only a single user U for convenience of explanation, but actually there are a plurality of users U in some cases. When there are a plurality of users U, each of the users U can operate a different user terminal 2 and a different thermometer 3.

For example, in this embodiment, this information processing system S performs the following operations (processes).

First, as a basic operation, each time the thermometer 3 measures the user U's basal body temperature after awakening, the user terminal 2 stores and manages information including at least the measurement date and time, and the measurement (the measured basal body temperature) as a measurement log.

These measurement logs are managed in, but not particularly limited to, the user terminal 2, and may be managed in any place including the server 1.

Usually, there is a relationship between a human's basal body temperature and how many hours he or she has slept. That is, too little sleep tends to lower the basal body temperature. Thus, in order to correctly measure the user U's basal body temperature, it is desirable for the user U to have adequate hours of sleep, which are not too short, before taking the basal body temperature.

Also in order to make a user's basal body temperatures to be measured less variable, it is considered desirable to take the basal body temperature around the same time every time.

Thus, it is desirable for a user to take the basal body temperature around the same time every time after having adequate hours of sleep.

For these reasons, based on the times at which the user U's basal body temperatures were measured, the server 1 sets, as a base measurement time, a time used as a basis for the user U to take the basal body temperature. By using this base measurement time as a guide, the user U can take the basal body temperature around the same time every time.

The server 1 estimates the user U's most recent sleep duration, and causes an alarm to sound when the estimated sleep duration exceeds a predetermined threshold value. The threshold value is not particularly limited and may be freely set. It is preferable to set the threshold value, based on adequate hours of sleep required to measure the basal body temperature. This is because if the user U's most recent sleep duration exceeds the predetermined threshold value, it means that the user U has gotten adequate hours of sleep required to correctly measure the basal body temperature.

Thus, when the user U's sleep duration exceeds the predetermined threshold value, the server 1 performs control for causing an alarm to sound at the base measurement time. As a result of this control, an alarm prompting the user U, who has gotten enough hours of sleep to correctly measure the basal body temperature, to take the basal body temperature is sounded around the same time every time.

This can effectively and reliably prevent the user U's failure to take the basal body temperature.

Figure 2:
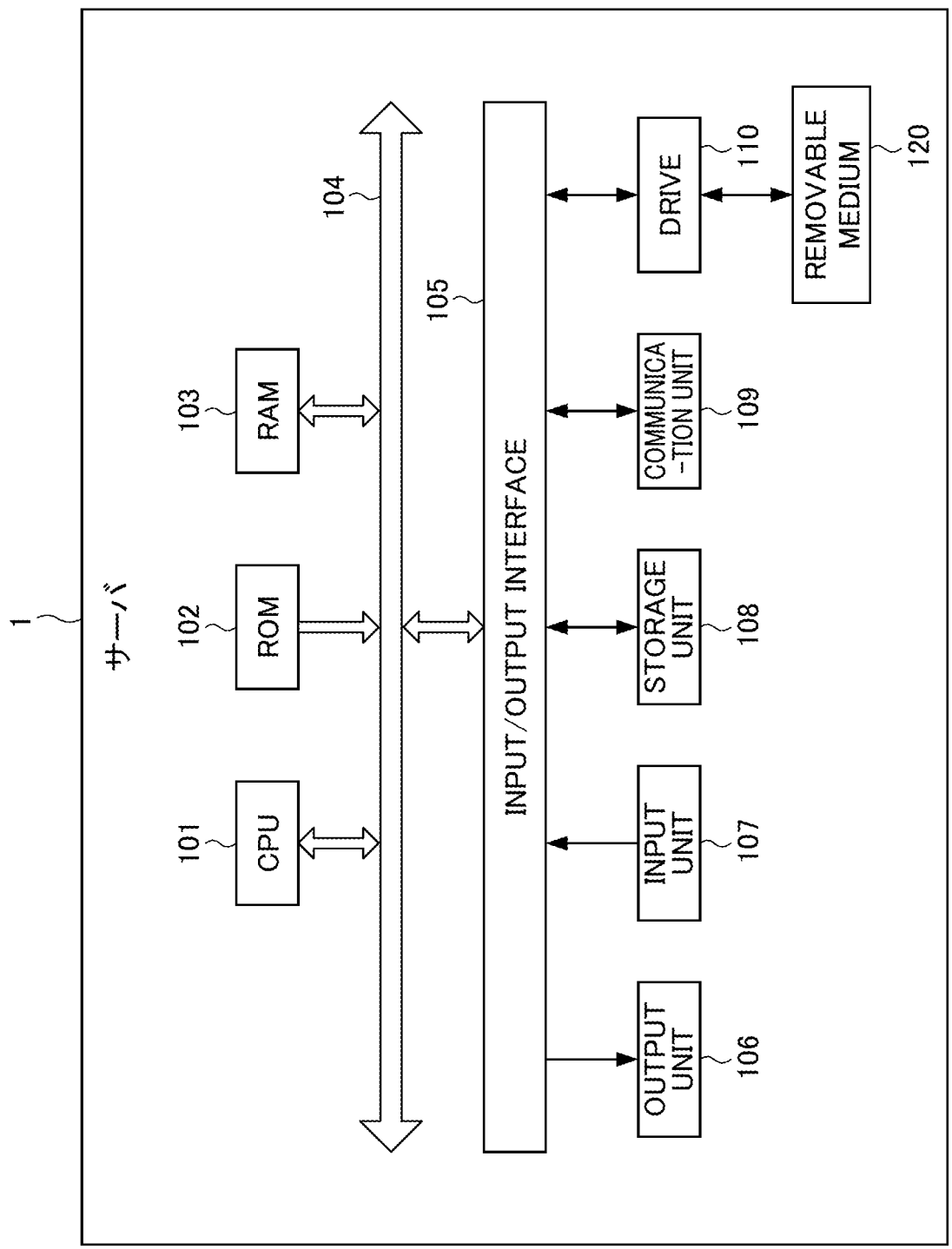
FIG. 2 is a block diagram showing a hardware configuration of a server included in the information processing system of FIG. 1.

FIG. 2 is a block diagram showing a hardware configuration of the server 1 included in the information processing system S of FIG. 1.

The server 1 includes a central processing unit (CPU) 101, a read only memory (ROM) 102, a random access memory (RAM) 103, a bus 104, an input/output interface 105, an output unit 106, an input unit 107, a storage unit 108, a communication unit 109, and a drive 110.

The CPU 101 performs various processes in accordance with programs stored in the ROM 102 or programs loaded from the storage unit 108 to the RAM 103.

The RAM 103 also stores, for example, data required for the CPU 101 to perform various processes, as appropriate.

The CPU 101, the ROM 102, and the RAM 103 are connected to each other via the bus 104. The input/output interface 105 is also connected to this bus 104. The output device 106, the input device 107, the storage unit 108, the communication unit 109, and the drive 110 are connected to the input/output interface 105.

The output device 106, which includes a display and a speaker, outputs various types of information as images and sounds.

The input unit 107, which includes a keyboard and a mouse, inputs various types of information.

The storage unit 108, which includes a hard disk and a dynamic random access memory (DRAM), stores various types of data.

The communication unit 109 communicates with other devices (the user terminal 2 in the example of FIG. 1) via the network N including the Internet.

A removable medium 120, such as a magnetic disk, an optical disk, a magneto-optical disk, or a semiconductor memory, is mounted in the drive 110 as appropriate. Programs read from the removable medium 120 by the drive 110 are installed on the storage unit 108 as needed.

The removable medium 120 can also store various types of data stored in the storage unit 108, as with the storage unit 108

Although not shown, the user terminal 2 in the information processing system S of FIG. 1 has essentially the same hardware configuration as FIG. 2 shows.

Figure 3:
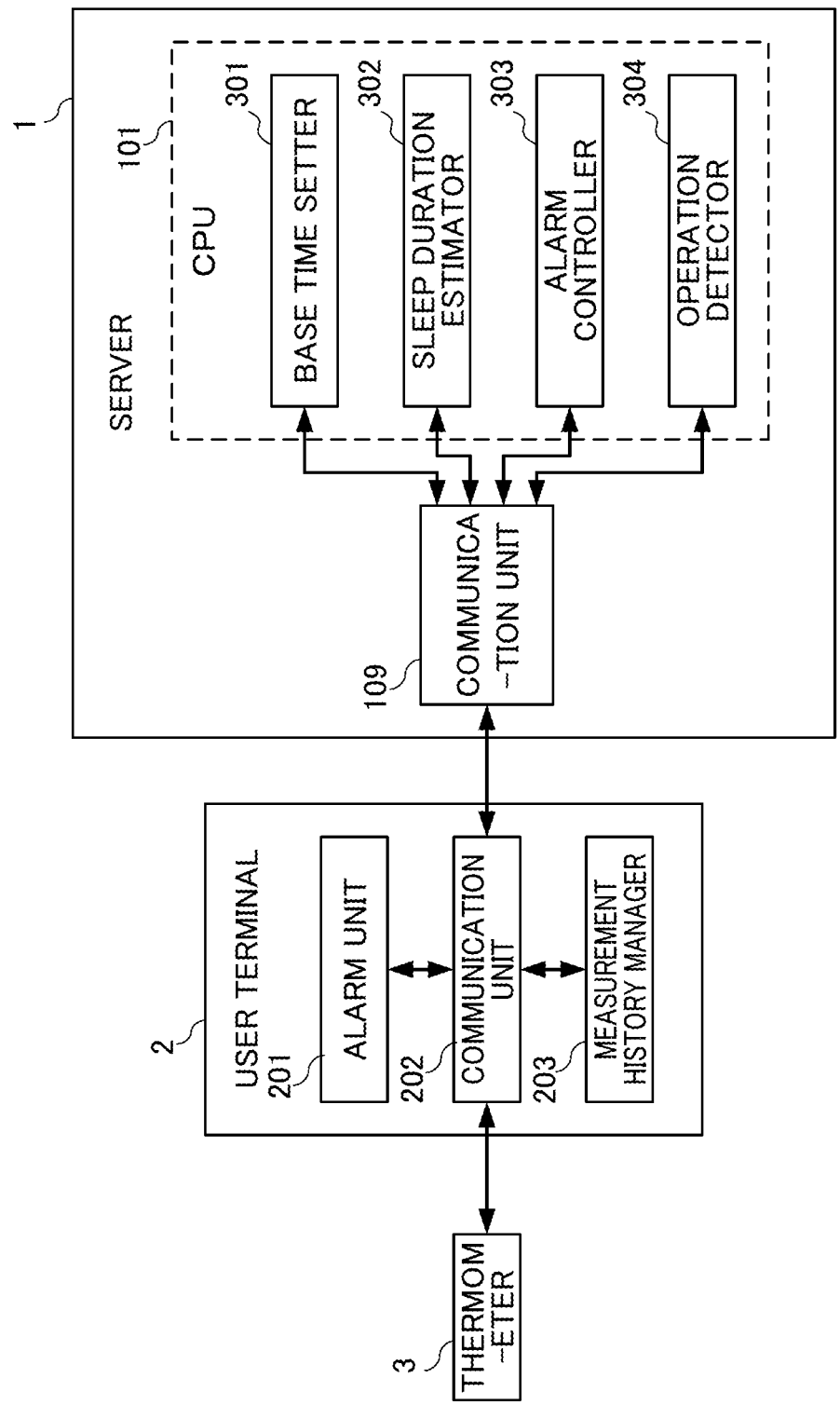
FIG. 3 is a functional block diagram showing an example functional configuration of the server and a user terminal included in the information processing system of FIG. 1.

FIG. 3 is a functional block diagram showing an example functional configuration of the server 1 and the user terminal 2 included in the information processing system S of FIG. 1.

As shown in FIG. 3, the user terminal 2 functions as an alarm unit 201, a communication unit 202, and a measurement history manager 203.

The CPU 101 of the server 1 functions as a base time setter 301, a sleep duration estimator 302, an alarm controller 303, and an operation detector 304.

In the user terminal 2, the alarm unit 201 sounds an alarm when a predetermined trigger is given (e.g., when a specified time comes).

The communication unit 202 exchange various types of information with the server 1 over the network N and also exchanges various types of information with the thermometer 3 via given communication means, such as Bluetooth□.

Each time the thermometer 3 measures the user U's basal body temperature, the measurement history manager 203 receives the measurement via the communication unit 202, and then stores and manages it as a measurement log.

In the server 1, the base time setter 301 sets a base measurement time, based on the measurement times at which the user U's body temperatures after awakening were measured.

In this embodiment, assume that "the measurement times at which the user U's body temperatures after awakening were measured" are obtained from the measurement logs managed by the measurement history manager 203 of the user U's user terminal 2.

How the base time setter 301 sets the base measurement time is not particularly limited.

For example, the base time setter 301 can find a base time, based on the measurement times included in the measurement logs for the user U's body temperatures after awakening that were regularly measured. The base time setter 301 can then set, as a base measurement time, a time that is a predetermined period of time or more after the base time. The predetermined period of time is determined based on the average value or the mode value of the measurement times and on the standard deviation of the measurement times.

In this case, if there is a small difference among the measurement times at which the user U took the basal body temperatures, the predetermined period of time, which is determined based on the average value or the mode value of the measurement times and on the standard deviation of the measurement times, becomes relatively short. This can cause an alarm to sound early. On the other hand, if there is a large difference among the measurement times at which the user U took the basal body temperatures, the predetermined period of time, which is determined based on the average value or the mode value of the measurement times and on the standard deviation of the measurement times, becomes relatively long. This can make an alarm less likely to be sounded before a time set as the base measurement time.

Figure 4:
FIG. 4 is a diagram schematically showing how the server of FIG. 3 sets a base measurement time.

FIG. 4 is a diagram schematically showing how the server 1 of FIG. 3 sets a base measurement time.

As described above, each time the user U takes the basal body temperature with the thermometer 3 after waking up, the measurement history manager 203 stores and manages, as a measurement log, information including at least the "date" on which of the basal body temperature was taken, the "measurement time", and the "basal body temperature" as the measurement.

The base time setter 301 can set the user U's base measurement time, based on the "measurement times" included in the measurement logs thus managed.

For example, the example of FIG. 4 shows measurement logs for the user U's basal body temperatures taken every day for a week from June 6 (Mon.) to June 12 (Sun.).

The base time setter 301 sets the user U's base measurement time, for example, to 7:00 a.m., based on the measurement times included in the measurement logs shown in FIG. 4.

Referring back to FIG. 3, the sleep duration estimator 302 estimates the user U's most recent sleep duration.

How the sleep duration estimator 302 estimates the sleep duration is not particularly limited. For example, this embodiment uses a method for estimating the sleep duration to be the length of time that has elapsed since the user U's most recent operation on the user terminal 2.

To do this, the server 1 in this embodiment includes the operation detector 304. The operation detector 304 detects any operation performed on the user terminal 2.

Thus, in this embodiment, the sleep duration estimator 302 estimates the sleep duration to be the time interval between when the operation detector 304 detected the most recent operation and the current time.

When the sleep duration estimated by the sleep duration estimator 302 exceeds the predetermined threshold value, the alarm controller 303 performs various controls for causing the user terminal 2 to sound an alarm at the base measurement time set by the base time setter 301 (for giving such a trigger to the alarm unit 201).

Figure 5A:
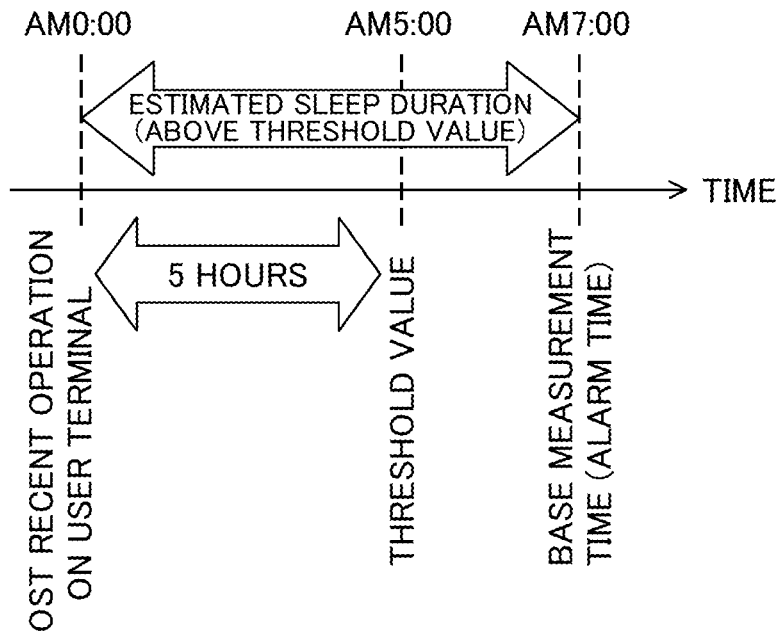
FIGS. 5A and 5B are diagrams schematically illustrating how the server of FIG. 3 controls the sounding of alarms.
Figure 5B:
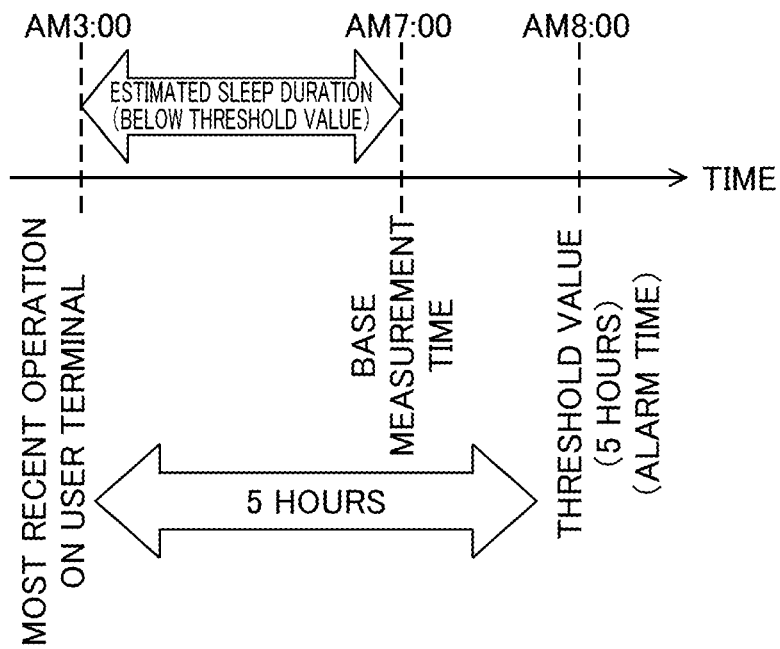

FIGS. 5A and 5B are diagrams schematically illustrating how the server of FIG. 3 controls the sounding of alarms.

In the examples of FIGS. 5A and 5B, assume that the base measurement time is preset to 7:00 a.m. by the base time setter 301, as in the above example of FIG. 4. Also assume that the threshold value is set to 5 hours of sleep, which are required to correctly measure basal body temperatures.

In the example of FIG. 5A, the sleep duration estimator 302 estimates that user U's sleep duration to be 7 hours from 0:00 a.m., at which the user U's most recent operation on the user terminal 2 was performed, to 7:00 a.m., which is the base measurement time.

The alarm controller 303 determines that the estimated sleep duration (7 hours) exceeds the predetermined threshold value (5 hours) and then performs control for causing an alarm to sound at the base measurement time 7:00 a.m.

On the other hand, in the example of FIG. 5B, the user U's most recent operation on the user terminal 2 was performed at 3:00 a.m. Thus, the sleep duration estimator 302 estimates that user U's sleep duration to be 4 hours from 3:00 a.m. to the base measurement time 7:00 a.m.

The alarm controller 303 determines that the estimated sleep duration (4 hours) is less than the predetermined threshold value (5 hours) and then performs control for forbidding an alarm to sound at the base measurement time 7:00 a.m.

As described above, in order to correctly measure the user U's basal body temperature, it is preferable to cause an alarm to sound after the user U has gotten usually required hours of sleep, specifically, for example 5 hours set as the threshold value in the examples of FIGS. 5A and 5B. Thus, in this embodiment, if an alarm is forbidden to sound at the base measurement time, then the alarm controller 303 causes the alarm to sound at a predetermined time that is the time when the user's most recent sleep duration will exceed the threshold value (5 hours) or after.

In the example of FIG. 5B, the alarm controller 303 performs control for causing an alarm to sound at 8:00 a.m. when the estimated sleep duration exceeds the threshold value (5 hours).

If an alarm is forbidden to sound at the base measurement time, whether to cause the alarm to sound after that is not particularly limited, and any other algorithm can be used. If a predetermined algorithm that causes the alarm to sound after that is used, the timing of sounding the alarm is not limited to the example of FIG. 5B and can be set to any timing.

The following describes a series of steps (hereinafter, referred to as an "alarm sounding process") through which the server 1 causes the user terminal 2 to sound an alarm.

Figure 6:
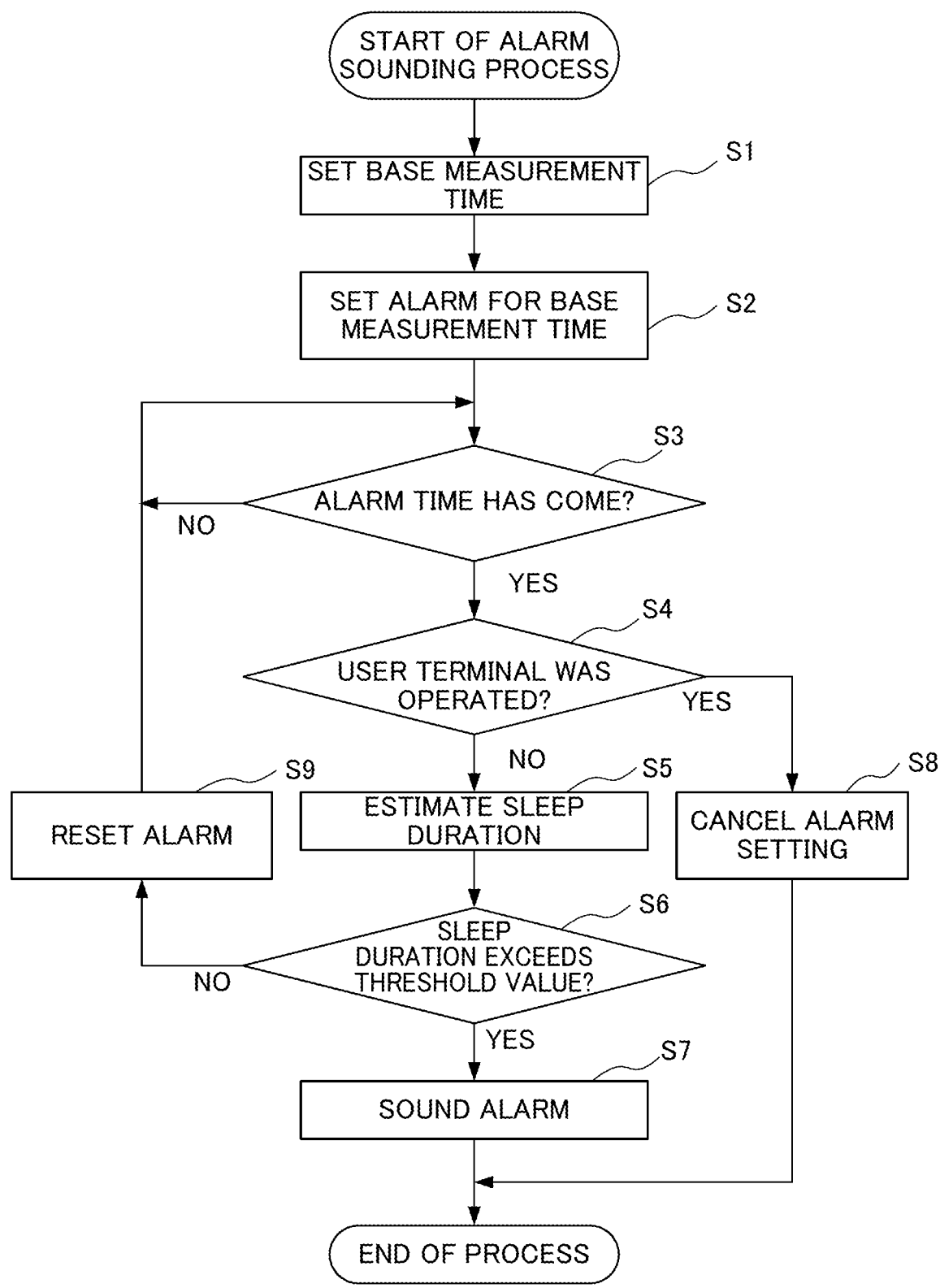
FIG. 6 is a flowchart illustrating an alarm sounding process performed by the server of FIG. 3.

FIG. 6 is a flowchart illustrating the alarm sounding process performed by the server 1 of FIG. 3.

In Step S1, the base time setter 301 of the server 1 sets a base measurement time, based on the measurement times at which the user U's body temperatures after awakening were measured.

In Step S2, the alarm controller 303 sets an alarm for the base measurement time.

In Step S3, the alarm controller 303 determines whether the current time is the alarm time.

If the current time is not yet the alarm time (NO in Step S3), the process returns to Step S3. That is, the determination in Step S3 is repeated until the current time becomes the alarm time. After that, if the current time becomes the alarm time (YES in Step S3), the process proceeds to Step S4.

In Step S4, the alarm controller 303 determines whether the user terminal 2 was operated before the alarm time comes (before YES in Step S3).

Step S4 is the step of determining whether the user U transitioned from a sleeping state to a waking state before the alarm time.

How to determine whether the user transitioned from the sleeping state to the waking state is not particularly limited. The example of FIG. 6 uses a method for estimating that the user U transitioned from the sleeping state to the waking state when the user U in the sleeping state operated the user terminal 2. In order to use this method, the example of FIG. 6 includes Step S4.

The user U in the waking state usually repeats operations on the user terminal 2 in a relatively short span of time. Thus, it is preferable to determine in Step S4 whether the user terminal 2 was operated between when the alarm controller 303 checked that the user was in the sleeping state and the alarm time (e.g., the base measurement time).

For this reason, in this embodiment, the sleep duration estimator 302 estimates that the user is in the sleeping state when no operation is performed on the user terminal 2 for a predetermined duration of time.

The sleep duration estimator 302 then checks whether there is any log data for operations on the user terminal 2 between when the user went into this sleeping state and the alarm time.

If there is at least one piece of log data for operations on the user terminal 2 (YES in Step S4), the process proceeds to Step S8. Step S8 and subsequent steps will be described later.

On the other hand, if there is no log data for operations on the user terminal 2 (NO in Step S4), that is, the user U stays in the sleeping state (the user U does not yet go into the waking state), the process proceeds to Step S5.

In Step S5, the sleep duration estimator 302 estimates the user U's most recent sleep duration.

In Step S6, the alarm controller 303 determines whether the user U's sleep duration estimated in Step S5 exceeds a predetermined threshold value.

If the estimated sleep duration exceeds the predetermined threshold value (YES in Step S6), that is, the user U has slept over the predetermined threshold value (the user has gotten enough hours of sleep to take the basal body temperature) at the alarm time (e.g., the base measurement time), the process proceeds to Step S7.

In Step S7, the alarm controller 303 performs control for causing the user terminal 2 to sound an alarm.

This concludes the alarm sounding process.

The following describes an example screen displayed on the user terminal 2 when an alarm is sounded by the user terminal 2 though this alarm sounding process.

Figure 7:
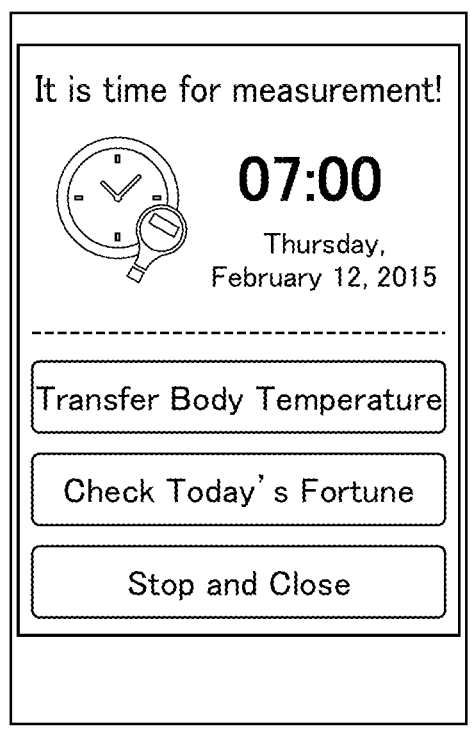
FIG. 7 is a diagram showing an example screen displayed on the user terminal of FIG. 3, which is sounding an alarm, as a result of the alarm sounding process of FIG. 6.

FIG. 7 is a diagram showing an example screen displayed on the user terminal 2 when an alarm sounds.

When being sounded by the alarm unit 201 of the user terminal 2 under the control of the alarm controller 303 of the server 1, an alarm causes the user U who is asleep to perceive that the base measurement time has come and can surely wake the user U.

In addition, the user terminal 2 in this embodiment displays such a screen as exemplified in FIG. 7 at the same time as the alarm sounds, thus prompting the user U to perform operations for taking the basal body temperature and for sending the measurement to the server 1.

Specifically, the screen exemplified in FIG. 7 displays the message "It is time for measurement!", which informs the user U that the measurement time has come, and the measurement date and time (7:00 Thursday, Feb. 12, 2015). The screen also displays a "Transfer body temperature" software button for transferring a body temperature from the thermometer 3 to the user terminal 2 and a "Stop and Close" software button for stopping the alarm from sounding.

Information included in the screen is not particularly limited to what prompts the user U to take the basal body temperature and to send the measurement. The information can include, for example, other information that appeals to the user U (a "Check today's fortune" software button, in the example of FIG. 7).

The above describes a flow of a normal case of the alarm sounding process where the user U has slept over the predetermined threshold value (the user has gotten enough hours of sleep to take the basal body temperature) at the base measurement time.

The following describes different cases of the alarm sounding process from the normal case.

Such cases different from the normal case include a case where the user wakes up before the base measurement time, in other words, a case where the user U transitions from the sleeping state to the waking state before the base measurement time.

In this case, the following steps are performed in the example of FIG. 6. If the operation detector 304 detects an operation on the user terminal 2 before the current time becomes the base measurement time (the alarm time) (YES in Step S4), it is determined that the user U went into the waking state and the process proceeds to Step S8.

In Step S8, the alarm controller 303 cancels the alarm setting. This concludes the alarm sounding process.

The process performed in the case where the user wakes up before the base measurement time is not particularly limited to the example of FIG. 6, and any other process can be used.

For example, whether the user is in the waking state or in the sleeping state, the alarm controller 303 may always cause an alarm to sound if a certain condition (e.g., the condition that the sleep duration exceeds the threshold value and then the base measurement time comes) is met.

However, if the user is already in the waking state, it is preferable that the server 1 cancel the alarm setting as shown in the example of FIG. 6.

On the other hand, if an operation is performed on a user terminal 2 (if the user goes into the waking state) before the base measurement time while the user U is in the sleeping state, the alarm controller 303 may determine whether to cancel the alarm setting also based on the sleep duration, without always canceling the alarm setting as shown in the example of FIG. 6.

For example, when an operation is performed on the user terminal 2 before the base measurement time while the user U is in the sleeping state, the alarm controller 303 may cause an alarm to sound if the user U's most recent sleep duration exceeds the predetermined threshold value at that point, and may cancel the alarm setting at the base measurement time if the user U's most recent sleep duration is below the predetermined threshold value at that point.

In the example of FIG. 6, an operation performed on the user terminal 2 while the user is in the sleeping state indicates that the user has transitioned from the sleeping state to the waking state. However, in some cases, another person except the user U may operate the user terminal 2 while the user U is in the sleeping state. The server 1 may perform the following process for such cases.

As described above, the sleep duration estimator 302 estimates that the user U is in the sleeping state when no operation is performed on the user terminal 2 for a predetermined duration of time.

If an operation is performed on the user terminal 2 before a base setting time while the user U is in the sleeping state, the server 1 presents a message asking the user U whether he or she has woken up.

If an operation indicating that the user U has woken up is performed on the user terminal 2 after the message is presented, the alarm controller 303 determines whether to sound an alarm, based on the relationship between that point and the base measurement time and on the relationship between the sleep duration at that time and the threshold value.

On the other hand, if an operation indicating that the user U has not yet woken up is performed on the user terminal 2 or user U has not operate the user terminal 2, it is highly likely that another person operated the user terminal 2. That is, it is highly likely that the user U is in the sleeping state. Thus, in such a case, the sleep duration estimator 302 continues calculations for estimating the sleep duration, and causes an alarm to sound after the estimated sleep duration exceeds the predetermined threshold value.

The above describes the process performed when the user terminal 2 is operated before the base measurement time, as an example case different from the normal case of the alarm sounding process.

The following describes a process performed when the sleep duration is still below the predetermined threshold value even at the base measurement time (when the user has not gotten enough hours of sleep yet), as another example case different from the normal case of the alarm sounding process.

In this case, the following steps are performed in the example of FIG. 6.

If the base measurement time, for which an alarm was set, comes (YES in Step S3) and the user terminal 2 has not been operated yet (NO in Step S4), the sleep duration is estimated (Step S5). If the estimated sleep duration is still below the predetermined threshold value (NO in Step S6), the process proceeds to Step S9.

In Step S9, the alarm controller 303 resets the alarm. Specifically, the alarm controller 303 resets the alarm for a predetermined time that is the time when the user's most recent sleep duration will exceed the predetermined threshold value or after.

This causes the process to return to Step S3, and then Step S3 and subsequent steps are repeated.

Although the above describes an embodiment of the present invention, the present invention is not limited to the above-described embodiment. It should be understood that any modification, improvement, or the like that can achieve the objects of the present invention falls within the scope of the invention.

For example, in the above embodiment, the timing of setting an alarm is a timing in the Step S2 of FIG. 2. However, it is not particularly limited, and any timing immediately before (at almost the same time when) an alarm sounds in Step S7 can be used.

For example, the alarm controller 303 may set the alarm for the base measurement time at the timing when both a first condition that the base measurement time comes (YES in Step S3) and a second that the sleep duration exceeds the threshold value (YES in Step S6) are satisfied.

For example, how an alarm sounds is not particularly limited. For example, dedicated application software may cause an alarm to sound. Alternatively, the user terminal 2 may cause an alarm to sound using an alarm function provided in it.

Figure 8:
FIG. 8 is a diagram showing a specific example of how the server of FIG. 3 changes status information for setting alarms.

In the latter case, for example, as shown in FIG. 8, the functions of managing one or more pieces of alarm data and of sounding an alarm, based on alarm data in which status information is "ON", can be used as the alarm function provided in the user terminal 2.

Each piece of alarm data is a set of data including a predetermined identifier (alarm ID), an alarm time, and status information indicating that an alarm is "ON" or "OFF".

When using such a function provided in the user terminal 2, the alarm controller 303 of FIG. 3 basically generates and registers new alarm data for sounding the next alarm.

However, simply generating and registering new alarm data every time may cause duplicate registration of alarm data having the same content as that registered in the past and result in unnecessary consumption of memory.

In order to avoid this, the alarm controller 303 can reuse, if previously registered alarm data has the same content as new alarm data to be registered next, the previously registered alarm data without registering the new alarm data.

The "reuse" means that the status information in the previously registered alarm data is changed from "OFF" to "ON".

The following specifically describes that with reference to FIG. 8.

FIG. 8 is a diagram showing a specific example of how the alarm controller 303 of FIG. 3 changes status information.

In order to control the sounding of an alarm, the alarm controller 303 basically generates alarm data including an alarm time, a predetermined identifier (alarm ID), and status information indicating that an alarm is "ON" or "OFF", and then newly registers the data alarm in the user terminal 2.

The status information in the newly registered alarm data is initially set to "ON". This causes the alarm to sound at the alarm time identified by the alarm data. When the alarm stops sounding, the status information in the alarm data is set to "OFF".

Thus, before registering the new alarm data, the alarm controller 303 checks whether there is any alarm data including a time that is the same as an alarm time to be registered next among existing pieces of alarm data set to "OFF".

If there is alarm data including a time that is the same as the alarm time to be registered next, the alarm controller 303 changes the status information in the alarm data from "OFF" to "ON". In this case, the alarm controller 303 does not register the new alarm data, thus avoiding unnecessary consumption of memory.

Specifically, for example, as illustrated in the upper diagram of FIG. 8, three pieces of alarm data (alarm IDs "0001" to "0003") are already registered and managed. In the alarm data including the alarm ID "0001", the alarm time is "every morning 7:00" and the status information is "ON". In the alarm data including the alarm ID "0002", the alarm time is "7:20" and the status information is "OFF". In the alarm data including the alarm ID "0003", the alarm time is "5:30" and the status information is "OFF".

Here, assume that the alarm controller 303 is setting the next alarm for "7:20".

In this case, the alarm controller 303 finds the registered alarm data including the alarm ID "0002", in which the alarm time is set to "7:20". As illustrated in the lower diagram of FIG. 8, the alarm controller 303 then changes the status information in the alarm data from "OFF" to "ON".

In addition, in order to prevent an alarm from sounding at "7:00" immediately before "7:20", the alarm controller 303 changes the status information in the registered alarm data including the alarm ID "0001", in which the alarm time is set to "every morning 7:00", from "ON" to "OFF".

That is summarized as follows. In some cases, the user terminal 2 manages whether to sound alarms, using sets of data (alarm data) each including a predetermined identifier, an alarm time, and status information indicating that an alarm is "ON" or "OFF".

In such a case, if the already managed sets include a set having an alarm time that is the same as the base measurement time (the next alarm time), the alarm controller 303 changes the status information included in the set to "ON".

This can prevent unnecessary alarm data from being newly registered, thus avoiding unnecessary consumption of memory.

Also for example, the base measurement time is fixed in the above embodiment, but is not particularly limited to this.

That is, after setting a base measurement time, the base time setter 301 may further perform a process for resetting the base measurement time at a predetermined timing. In other words, even once setting a base measurement time, the base time setter 301 may dynamically change the base measurement time as the time of the user U taking the basal body temperature changes, for example, with changes in the user U's environment.

This enables the user U to always take the basal body temperature at the right timing even when the user U's environment or the like changes.

Also for example, the hardware configuration shown in FIG. is merely an example for achieving the objects of the present invention and is not particularly limited.

FIG. 3 shows merely an example functional block diagram and is not particularly limited. Specifically, the information processing device only needs to have functions capable of performing the above series of steps as a whole. What function blocks to use to implement these functions is not particularly limited to the example of FIG. 3.

Where to place the function blocks is not limited to FIG. 3, and they may be freely placed.

Each of the function blocks may be implemented in hardware, software, or a combination thereof.

For example, at least some of the functions, including the alarm controller 303 of the server 1, can be placed in the user terminal 2. On the other hand, at least some of the functions, including the measurement history manager 203 of the user terminal 2, can be placed in the server 1.

When the process of each function block is performed by software, programs constituting the software are installed on, for example, a computer from a network or a recording medium.

The computer may be a computer integrated into dedicated hardware. The computer may be a computer that has various programs installed on it and is capable of performing various functions, such as a general-purpose smartphone or personal computer as well as a server.

Examples of recording mediums that store these programs include a removable medium that is distributed separately from a main unit in order to provide each user with the programs and a recording medium that is built in a main unit and provided to each user.

To summarize the above, an information processing system to which the present invention is applied only needs to be configured as follows and is susceptible of embodiment in many different forms.

The information processing system (e.g., the information processing system S of FIG. 1 includes base time setting means (e.g., the base time setter 301 of FIG. 3), sleep duration estimation means (e.g., the sleep duration estimator 302 of FIG. 3), and alarm control means (e.g., the alarm controller 303 of FIG. 3).

The base time setting means sets, as a base measurement time, a time used as a basis for a user (e.g., the user U of FIG. 1) to take the user's body temperature after awakening, based on the times at which the user's body temperatures were measured.

The sleep duration estimation means estimates the user's most recent sleep duration.

When the user's most recent sleep duration exceeds a predetermined threshold value, the alarm control means causes an alarm to sound at the base measurement time.

This can effectively prevent the user's failure to take the basal body temperature.

The sleep duration estimation means can estimate the sleep duration to be the time interval between the user's most recent operation on the user's mobile terminal (e.g., the user terminal 2 of FIG. 1) and the base measurement time.

Thus, the sleep duration can be easily estimated using simple configuration and logic.

When no operation is performed on the user's mobile terminal for a predetermined duration of time, the sleep duration estimation means further estimates that the user is in a sleeping state.

If an operation is performed on the mobile terminal before the base measurement time in the sleeping state, the alarm control means can cancel a process for causing an alarm to sound at the base measurement time.

This can prevent an alarm from sounding unnecessarily even if the user U wakes up before the set alarm time (the base measurement time).

When no operation is performed on the user's mobile terminal for a predetermined duration of time, the sleep duration estimation means further estimates that the user is in a sleeping state.

When an operation is performed on the mobile terminal before the base measurement time in the sleeping state, the alarm control means can cause an alarm to sound if the user's most recent sleep duration exceeds a predetermined threshold value at that point, and cancel a process for causing an alarm to sound at the base measurement time if the user's most recent sleep duration is below a predetermined threshold value at that point.

This can prevent the user U from taking the basal body temperature before getting enough hours of sleep.

If the sleep duration does is below the predetermined threshold value at the base measurement time, the alarm control means can further cause an alarm to sound at a predetermined time that is the time when the user's most recent sleep duration will exceed a predetermined threshold value or after.

This can sound an alarm at the right timing even if the base measurement time comes before the user's estimated sleep duration exceeds the threshold value.

If an operation is performed on the mobile terminal between the base measurement time and the predetermined time in the sleeping state, the alarm control means can cancel a process for causing an alarm to sound at the predetermined time.

This can prevent an alarm from sounding unnecessarily even if the user U wakes up before the set alarm time (the predetermined time after the alarm is reset).

After setting the base measurement time, the base time setting means can further perform a process for resetting the base measurement time at a predetermined timing.

This enables the user to always take the basal body temperature at the right timing even when the user's environment or the like changes.

The base time setting means can set the base measurement time, based on measurement times included in measurement logs for a user's body temperatures after awakening that were regularly measured.

This can more appropriately set the base measurement time.

The base time setting means can set, as the base measurement time, a time that is a predetermined period of time or more after a base time found based on the measurement times. The predetermined period of time is determined based on the average value or the mode value of the measurement times and on the standard deviation of the measurement times.

This can cause an alarm to sound early if there is a small difference among the measurement times at which the user took the basal body temperatures. This can make an alarm less likely to be sounded before a time set as the base measurement time if there is a large difference among the measurement times at which the user took the basal body temperatures.

Whether to sound the alarm is managed using sets of data (e.g., the pieces of alarm data of FIG. 8) each including a predetermined identifier, an alarm time, and status information indicating that an alarm is ON or OFF.

If the sets already managed include a set having an alarm time that is the same as the base measurement time, the alarm control means can change the status information included in the set to ON.

This can avoid unnecessary consumption of memory.

It should be noted that this specification includes not only a process in which steps written in programs stored in a recording medium are performed sequentially in their order but also a process in which some of the step are performed not sequentially but in parallel or separately.

For example, in the above alarm sounding process of FIG. 6, after the determination of whether the current time is the base measurement time (the determination in Step S3, which is referred to as a "first determination"), the determination of whether the user U's estimated sleep duration exceeds the predetermined threshold value (the determination in Step S6, which is referred to as a "second determination") is performed.

However, the first and second determinations each need only to be "YES" at the timing of control for causing the user terminal 2 to sound an alarm (when Step S7 is performed). Thus, the timing of each of the first and second determinations is not particularly limited.

For example, the first determination may be performed after the second determination. In this case, the base measurement time is set, the sleep duration is estimated, the second determination (the determination of whether the sleep duration exceeds the predetermined threshold value) is performed, and then the first determination (the determination of whether the current time is the base measurement time) is performed.

Consequently, an alarm is sounded if the base measurement time comes after the estimated sleep duration exceeds the threshold value, and the alarm is reset if the base measurement time comes before the estimated sleep duration exceeds the threshold value.

Alternatively, the first and second determinations may be performed in parallel.

In this specification, the term "system" means a comprehensive apparatus including a plurality of devices, a plurality of means, and the like.

REFERENCE SIGNS LIST 1 server
2 user terminal
3 thermometer
101 CPU
102 ROM
103 RAM
104 bus
105 input/output interface
106 output unit
107 input unit
108 storage unit
109 communication unit
110 drive
120 removable medium
201 alarm unit
202 communication unit
301 base time setter
302 sleep duration estimator
303 alarm controller
304 operation detector
401 message presentation controller
N network
S information processing system
U user The invention is:

1. An information processing system comprising:
   at least one memory configured to store computer program code; and
   at least one processor configured to access said computer program code and operate as instructed by said computer program code, said computer program code including:
      base time setting code configured to cause at least one of said at least one processor to, based on times at which body temperatures of a user were measured, set as a base measurement time, a time used as a basis for the user to take the user's body temperature after awakening;
      sleep duration estimation code configured to cause at least one of said at least one processor to estimate a first estimated sleep duration of the user; and
      alarm control code configured, at the base measurement time, to cause at least one of said at least one processor to:
         when the first estimated sleep duration of the user exceeds a predetermined threshold value, cause an alarm to sound at a first time, wherein the first time is the base measurement time, and
         when the first estimated sleep duration of the user does not exceed the predetermined threshold value, configure the alarm to not sound at the first time but to sound at a second time, wherein the second time is a time when a second estimated sleep duration of the user will exceed the predetermined threshold value.

2. The information processing system according to claim 1, wherein
   the sleep duration estimation code is configured to cause at least one of said at least one processor to estimate the first estimated sleep duration to be a time interval between a most recent operation of the user on a mobile terminal of the user and the base measurement time.

3. The information processing system according to claim 1, wherein
   when no operation is performed on a mobile terminal of the user for a predetermined duration of time, the sleep duration estimation code causes at least one of said at least one processor to further estimate that the user is in a sleeping state, and
   if an operation is performed on the mobile terminal before the base measurement time in the sleeping state, the alarm control code causes at least one of said at least one processor to cancel a process for causing the alarm to sound at the base measurement time.

4. The information processing system according to claim 1, wherein
   when no operation is performed on a mobile terminal of the user for a predetermined duration of time, the sleep duration estimation code causes at least one of said at least one processor to further estimate that the user is in a sleeping state, and
   when an operation is performed on the mobile terminal at a third time, wherein the third time is before the first time, the alarm control code causes at least one of said at least one processor to cause the alarm to sound if a third estimated sleep duration exceeds a predetermined threshold value at the first time, and cancels a process for causing the alarm to sound at the base measurement time if the third estimated sleep duration does not exceed the predetermined threshold value.

5. The information processing system according to claim 1, wherein
   if an operation is performed on a mobile terminal of the user between the first time and the second time, the alarm control code causes at least one of said at least one processor to cancel a process for causing the alarm to sound at the second time.

6. The information processing system according to claim 1, wherein
   after setting the base measurement time, the base time setting code causes at least one of said at least one processor to further perform a process for resetting the base measurement time at a predetermined timing.

7. The information processing system according to claim 1, wherein
   the base time setting code is configured to cause at least one of said at least one processor to set the base measurement time, based on a plurality of measurement times, wherein the plurality of measurement times are included in measurement logs for a user's body temperatures obtained regularly after awakening.

8. The information processing system according to claim 7, wherein
   the base time setting code is configured to cause at least one of said at least one processor to set, as the base measurement time, a time that is a predetermined period of time or more after a base time found based on the plurality of measurement times, and the predetermined period of time is determined based on an average value or an mode value of the plurality of measurement times and on a standard deviation of the measurement times.

9. The information processing system according to claim 1, wherein
   whether to sound the alarm is managed using sets of data each including a predetermined identifier, an alarm time, and status information indicating that the alarm is ON or OFF, and
   if the alarm time of a first set of the sets of data is the same as the base measurement time, the alarm control code causes at least one of said at least one processor to change the status information included in the first set of the sets of data to ON.

10. An information processing method performed by at least one processor in an information processing system, the information processing method comprising:
    setting, based on times at which body temperatures of a user were measured and as a base measurement time, a time used as a basis for the user to take the user's body temperature after awakening;
    estimating a first estimated sleep duration of the user;
    when the first estimated sleep duration of the user exceeds a predetermined threshold value, sounding an alarm at a first time, wherein the first time is the base measurement time; and
    when the first estimated sleep duration of the user does not exceed the predetermined threshold value, configuring the alarm to not sound at the first time but to sound at a second time, wherein the second time is a time when a second estimated sleep duration of the user will exceed the predetermined threshold value.

11. A non-transitory computer readable medium storing a program for causing a computer to execute a control process, the computer controlling at least one device belonging to an information processing system, the control process comprising:

setting, based on times at which body temperatures of a user were measured and as a base measurement time, a time used as a basis for the user to take the user's body temperature after awakening;

estimating a first estimated sleep duration of the user;

when the first estimated sleep duration of the user exceeds a predetermined threshold value, sounding an alarm at a first time, wherein the first time is the base measurement time; and when the first estimated sleep duration of the user does not exceed the predetermined threshold value, configuring the alarm to not sound at the first time but to sound at a second time, wherein the second time is a time when a second estimated sleep duration of the user will exceed the predetermined threshold value.

* * * * *